United States Patent
Stoltz et al.

(10) Patent No.: US 7,963,958 B2
(45) Date of Patent: *Jun. 21, 2011

(54) PORTABLE OPTICAL ABLATION SYSTEM

(75) Inventors: Richard Stoltz, Plano, TX (US); Jeff Bullington, Chuluota, FL (US)

(73) Assignee: Raydiance, Inc., Petaluma, CA (US)

( * ) Notice: Subject to any disclaimer, the term of this patent is extended or adjusted under 35 U.S.C. 154(b) by 438 days.

This patent is subject to a terminal disclaimer.

(21) Appl. No.: 11/894,867

(22) Filed: Aug. 21, 2007

(65) Prior Publication Data

US 2007/0293850 A1 Dec. 20, 2007

Related U.S. Application Data

(63) Continuation of application No. 10/916,017, filed on Aug. 11, 2004, now Pat. No. 7,361,171, which is a continuation-in-part of application No. PCT/US2004/015913, filed on May 19, 2004.

(60) Provisional application No. 60/471,971, filed on May 20, 2003, provisional application No. 60/471,922, filed on May 20, 2003, provisional application No. 60/503,578, filed on Sep. 17, 2003, provisional application No. 60/494,321, filed on Aug. 11, 2003.

(51) Int. Cl.
*A61B 18/18* (2006.01)

(52) U.S. Cl. ............. 606/10; 606/11; 607/88; 607/89; 359/333; 359/345

(58) Field of Classification Search .............. 606/3–12; 607/88, 89; 128/898; 216/65, 66, 87; 372/43.01, 372/50.11, 50.12; 359/333, 342–349
See application file for complete search history.

(56) References Cited

U.S. PATENT DOCUMENTS

| | | | |
|---|---|---|---|
| 6,156,030 A * | 12/2000 | Neev | 606/10 |
| 6,208,458 B1 * | 3/2001 | Galvanauskas et al. | 359/345 |
| 7,143,769 B2 * | 12/2006 | Stoltz et al. | 128/898 |
| 7,361,171 B2 * | 4/2008 | Stoltz et al. | 606/9 |
| 2005/0215985 A1 * | 9/2005 | Mielke et al. | 606/2 |
| 2006/0084957 A1 * | 4/2006 | Delfyett et al. | 606/12 |

* cited by examiner

*Primary Examiner* — Ahmed M Farah
(74) *Attorney, Agent, or Firm* — Carr & Ferrell LLP

(57) ABSTRACT

The present invention includes an apparatus and method of surgical ablative material removal "in-vivo" or from an outside surface with a short optical pulse that is amplified and compressed using either an optically-pumped-amplifier and air-path between gratings compressor combination or a SOA and chirped fiber compressor combination, wherein the generating, amplifying and compressing are done within a portable system.

24 Claims, 2 Drawing Sheets

PORTABLE OPTICAL ABLATION SYSTEM

CROSS-REFERENCE TO RELATED APPLICATIONS

This application is a continuation application of U.S. Patent Application Ser. No. 10/916,017 filed Aug. 11, 2004 now U.S. Pat. No. 7,361,171 and titled "Man-Portable Optical Ablation System" which is a continuation-in-part of Patent Application Serial No. PCT/US2004/015913 filed on May 19, 2004 and titled "Trains of Ablation Pulses from Multiple Optical Amplifiers" which claims the benefit of U.S. Provisional Patent Application Serial No. 60/471,971 filed on May 20, 2003 and titled "Stretched Optical Pulse Amplification and Compression," U.S. Provisional Patent Application Serial No. 60/471,922 filed on May 20, 2003 and titled "Laser Machining," and U.S. Provisional Patent Application Serial No. 60/503,578 filed on Sep. 17, 2003 and titled "Controlling Optically-Pumped Optical Pulse Amplifiers;" this application also claims the benefit of U.S. Provisional Patent Application Serial No. 60/494,321 filed on Aug. 11, 2003 and titled "Man-Portable Optical Ablation System." The disclosure of each of the aforementioned applications is incorporated herein by reference.

BACKGROUND OF THE INVENTION

1. Field of the Invention

The present invention relates in general to the field of light amplification and, more particularly to the altering the emission of an ablation beam for safety or control.

2. Description of Related Art

Ablative material removal is especially useful for medical purposes, either in-vivo or on the outside surface (e.g., skin or tooth), as it is essentially non-thermal and generally painless. Ablative removal of material is generally done with a short optical pulse that is stretched, amplified and then compressed. A number of types of laser amplifiers have been used for the amplification, including fiber-amplifiers. Fiber amplifiers have a storage lifetime of about 100 to 300 microseconds. While some measurements have been made at higher repetition rates, these measurements have shown an approximately linear decrease in pulse energy, and for ablations purposes, fiber amplifiers have been operated with a time between pulses of equal to or greater than the storage lifetime, and, thus, are generally run a rep rate of less than 3-10 kHz.

Laser machining can remove ablatively material by disassociate the surface atoms and melting the material. Laser ablation is done efficiently with a beam of short pulses (generally a pulse-duration of three picoseconds or less). Techniques for generating these ultra-short pulses (USP) are described, e.g., in a book entitled "Femtosecond Laser Pulses" (C. Rulliere, editor), published 1998,Springer-Verlag Berlin Heidelberg New York. Generally large systems, such as Ti:Sapphire, are used for generating ultra-short pulses (USP).

USP phenomenon was first observed in the 1970's, when it was discovered that mode-locking a broad-spectrum laser could produce ultra-short pulses. The minimum pulse duration attainable is limited by the bandwidth of the gain medium, which is inversely proportional to this minimal or Fourier-transform-limited pulse duration. Mode-locked pulses are typically very short and will spread (i.e., undergo temporal dispersion) as they traverse any medium. Subsequent pulse-compression techniques are often used to obtain USP's. Pulse dispersion can occur within the laser cavity so that compression techniques are sometimes added intra-cavity. When high-power pulses are desired, they are intentionally lengthened before amplification to avoid internal component optical damage. This is referred to as "Chirped Pulse Amplification" (CPA). The pulse is subsequently compressed to obtain a high peak power (pulse-energy amplification and pulse-duration compression).

SUMMARY OF THE INVENTION

Ablative material removal with a short optical pulse is especially useful for medical purposes and can be done either in-vivo or on the body surface, as it is essentially non-thermal and generally painless. Previously, ablative systems include optical benches weighing perhaps 1,000 pounds and occupying about 300 cubic feet. One embodiment of the present invention includes a system that weighs 100 pounds or less and occupies 2.5 cubic feet or less.

One embodiment of the present invention includes an amplifier and a pulse-compressor, enabling the invention to be man-portable. As used herein, the term "man-portable" generally means capable of being moved reasonably easily by one person. In one embodiment, the man-portable system is a wheeled cart. In another embodiment, the man-portable system is a backpack.

One embodiment of the man-portable unit includes a handheld probe, vest/backpack and two or more satchels. Other embodiments include handheld probe, vest and backpack. The unit can be relatively inexpensive and can be used by surgeons, doctors, dentists, scientists and emergency personnel in the field. However, those skilled in the art will recognize other uses for the invention. One embodiment can be used to perform emergency cutting of a victim, removal of material, etching, marking and cauterizing of wounds. One embodiment allows the beam to cut through any obstacles. In one embodiment, the system can be used to gain access, open, cut into, or other wise free a person or object. One embodiment can be used to cut the top of a vehicle loose, I-beam, wood, metal, plastic, carbon fiber, cloth or fiberglass.

As illustrated in FIG. 1, in one embodiment, the man-portable system, e.g. system 100, is used in a hospital. One embodiment includes a handheld probe, a vest and movable cart and power supplied from a wall plug. Another embodiment includes wheels on the cart. Another embodiment includes a 120 volt or 240 Volt power supply. One embodiment, the handheld probe, e.g. handheld probe 115, includes a beam-scanners and optical delivery fibers. In one embodiment, the vest can include an optical compressor, e.g. compressor 110. In another embodiment, optical amplifiers, e.g. amplifier 105, are positioned on or in the cart. In one embodiment, the cart includes a control module, e.g. control module 125; a control panel, e.g. control panel 130; a pulse generator, e.g. pulse generator 135; a power supply, e.g. power 120; a video camera, e.g. video camera 140; a video monitor, e.g. video monitor 145; an air flush system, e.g. air flush system 150; a suction system, e.g. suction system 155; and a marker beam generator, e.g. marker beam generator 160.

The concentration of pulse energy on a small spot enables the use of semiconductor-optical amplifiers or moderate-power fiber-amplifiers, as well as higher power Cr:YAG amplifiers. One embodiment includes a short initial optical pulse allows compression into a short pulse with an efficient and physically small compressor. Another embodiment has multiple semiconductor amplifiers or fiber amplifiers. In one embodiment, the amplifiers are Cr:YAG amplifiers. In one embodiment, the amplifier has a short (e.g., 1 nanosecond or less) initial optical pulse that undergoes controlled amplification and is then compressed into a short (sub-picosecond)

pulse, and the light pulse focused onto a small area, e.g., spot. In one embodiment, the area is between about 10 and about 50 microns in diameter. In one embodiment, the spot is scanned over an area to be ablated, wherein a controllable rate of ablation is achieved. One embodiment controls the amplifiers by controlling pulse power. One embodiment independently controls the ablation rate and pulse energy of multiple moderate-power amplifiers. In another embodiment, the amplifier is easily cooled. Thus, by the use of a combination of innovations, can now provide an efficient, reasonably priced, man-portable ablation system for medical and other purposes.

One embodiment includes a laser-amplifier and compressor that allow the system size is reduced, whereby the system to be man-portable. In one embodiment a semiconductor oscillator-driven pulse generator is used to generate a pulse between about ten picoseconds and about one nanosecond wavelength-swept-with-time. In one embodiment, the initial pulse is amplified by an optically-pumped amplifier. In one embodiment, the amplifier is an erbium-doped fiber amplifier or EDFA or a Cr:YAG amplifier. In one embodiment, the pulse is compressed by an air-path between gratings compressor or a Treacy grating air-grating compressor, wherein the compression creates a sub-picosecond ablation pulse. One embodiment has semiconductor optical amplifier (SOA) and a chirped fiber compressor, wherein the pulse is between about one to twenty nanosecond. In one embodiment, a semiconductor generates the initial pulse and a SOA preamplifier to amplify the initial pulse before introduction into the amplifier.

Different embodiments can be used for different applications depending on the specific needs of that application. One embodiment uses an optically-pumped—amplifier and air-grating-compressor to reduce cost, but another embodiment uses a SOA and chirped-fiber-compressor to produce an efficient and small system.

Ablative material removal can be done either in-vivo or on the body surface. As some materials ablate much faster than others and material is most efficiently removed at pulse energy densities about three times the materials ablation threshold. In one embodiment, the ablation rate is controlled. In one embodiment, the pulse energy density is controlled to produce a pulse energy densities about three times the materials ablation threshold. In one embodiment, the surgical ablation has a threshold of less than one Joule per square centimeter, however other embodiments have an ablation threshold of up to about two Joules per square centimeter.

Again, as materials ablate at different thresholds, efficient operation requires control of the pulse energy density. One embodiment controls the pulse energy, thereby controlling the pulse energy density. One embodiment uses a fiber amplifier operating at high repetition rates. One embodiment controls the pulse energy by controlling the optical pumping power. Another embodiment controls the pulse energy by controlling the pulse repetition rate. In another embodiment, the system is fine tuned by controlling optical pumping power.

In one embodiment, the pulse energy is controlled by repetition rate and optically pumped amplifier operating temperature is controlled through controlling optical pumping power. In one embodiment, the pulse energy of semiconductor optical amplifiers (SOAs) is adjusted by changing the amplifier current. In one embodiment, the pulse energy applied to the body is between about 2.5 and about 3.6 times the ablation threshold of the body portion being ablated.

In one embodiment, the ablation rate is controlled independent of pulse energy. The use of two or more amplifiers in a train mode (pulses from one amplifier being delayed to arrive at the spot one or more nanoseconds after those from another amplifier) allows step-wise control of ablation rate independent of pulse energy density. Without this delay, the efficiency is significantly reduced. The use of train-mode amplifiers in either type of system provides faster ablation, while providing greater cooling surface area to minimize thermal problems. In one embodiment, two or more amplifiers are operated in a train mode. At lower desired ablation rates, one or more amplifiers can be shut down. In one embodiment, one or more amplifiers in train mode are shut down.

As illustrated in FIG. 2, one embodiment of the present invention includes a method of material removal using surgical ablative, either from an in-vivo surface or from an outside surface with a short optical pulse that is amplified and then compressed, comprising: Step 200, generating an initial wavelength-swept-with-time pulse in a pulse generator within a man-portable system; Step 210, amplifying the initial pulse and then Step 220, compressing the amplified pulse within the man-portable system, wherein the amplifying and compression are done with either an optically-pumped-amplifier and air-path between gratings compressor combination, or a SOA and chirped fiber compressor combination; and Step 230, applying the compressed optical pulse to the surface.

In one embodiment, the amplifying and compressing is done with an optically-pumped-amplifier and an air-path between gratings compressor combination, wherein the pulses are between about ten picoseconds and about one nanosecond. In another embodiment, the amplifying and compressing is done with a SOA/chirped-fiber-compressor combination, wherein the initial pulses between about one and about twenty nanoseconds.

Another embodiment includes a method of ablative material removal, from a surface or with a short optical pulse that is amplified and then compressed, comprising: generating an initial pulse in a pulse generator; amplifying the initial pulse and then compressing the amplified pulse within the man-portable system, wherein the amplifying is done with either an optically-pumped-amplifier or a SOA; compressing the amplified pulse to a duration of less than one picosecond; and applying the compressed optical pulse to the surface, wherein the generating, amplifying and compressing are done within a man-portable system. In one embodiment, two or more optically-pumped optical amplifiers or SOA optical amplifiers are used in a train mode and the compressed optical pulse is applied to the surface in a small area spot, wherein, the spot area is between about ten and about 50 microns in diameter. In one embodiment, the pulse generator is semiconductor oscillator-driven.

In one embodiment, the amplifying and compressing is done with an optically-pumped-amplifier and air-path between gratings compressor combination, wherein the initial pulses are between about ten picoseconds and about one nanosecond. In one embodiment, the fiber amplifier is an erbium-doped or erbium/ytterbium fiber amplifier and the air-path between gratings compressor is a Treacy grating compressor. In one embodiment, two or more fiber amplifiers are used with one compressor. In another embodiment, the amplifier is an SOA and the compressor is a chirped optical fiber. In other embodiments, the pulse energy density and ablation rate are independently controlled. In other embodiments, the fiber amplifier and the amplifier temperature can be independently controlled.

High ablative pulse repetition rates are preferred and the total pulses per second (the total system repetition rate) from the one or more (train mode) optical amplifiers is preferably greater than 0.6 million. In one embodiment, the ablative pulse repetition rates are 0.6 million or more.

DETAILED DESCRIPTION OF THE INVENTION

Figure 1:
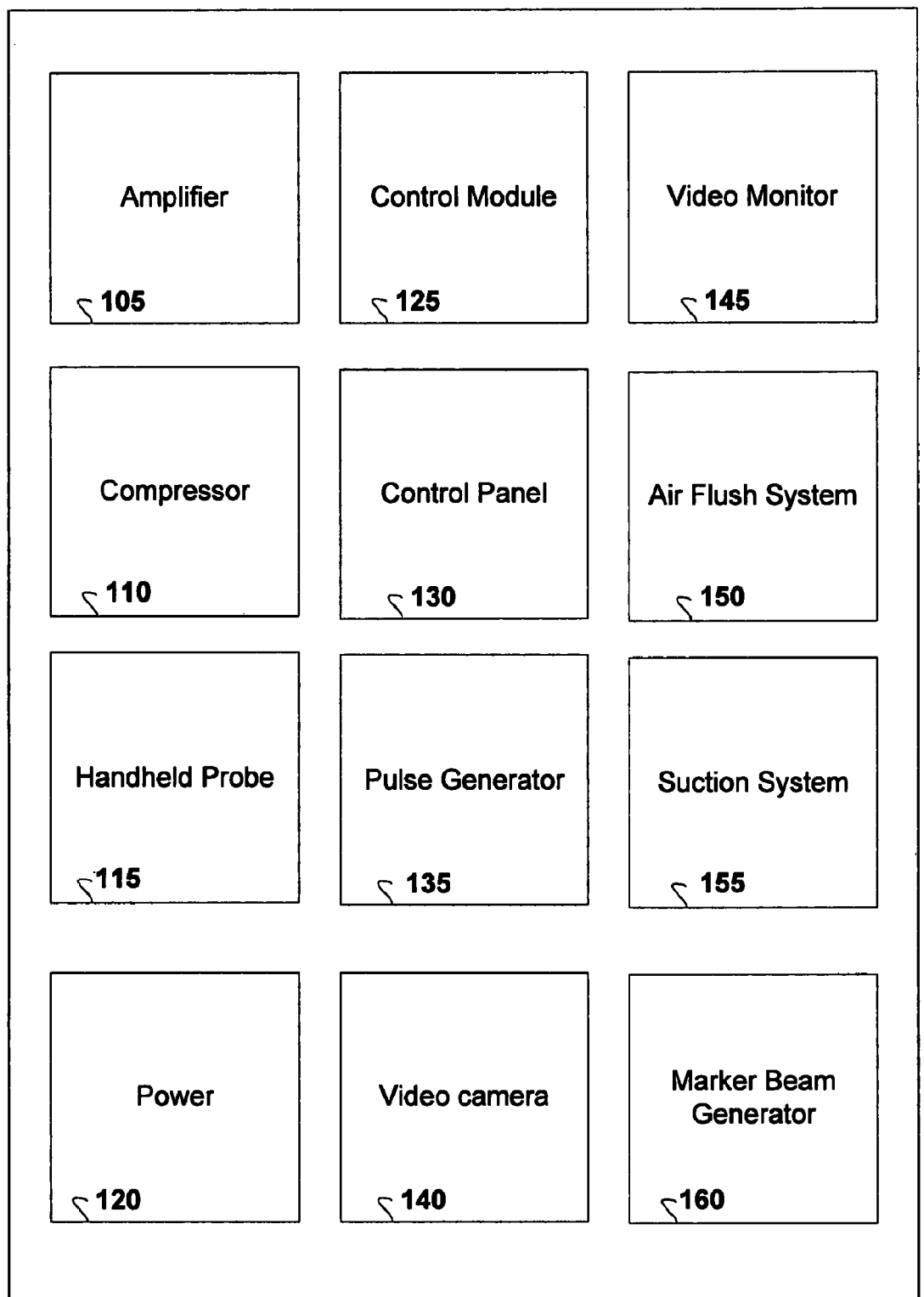
FIG. 1 is a block diagram of a system implementing one embodiment of the invention.
Figure 2:
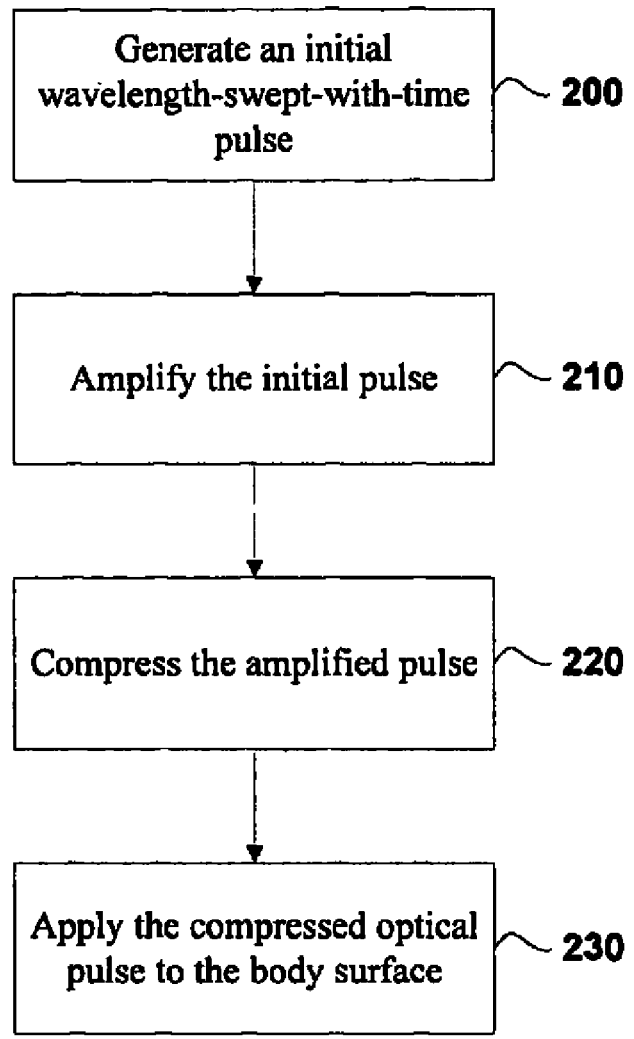
FIG. 2 is a flowchart illustrating the method used in one embodiment of the invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a," "an" and "the" are not intended to refer to only a singular entity, but include the general class of which a specific example may be used for illustration. The terminology herein is used to describe specific embodiments of the invention, but their usage does not delimit the invention, except as outlined in the claims.

Ablative material removal previously this has been done using systems with optical benches weighing perhaps 1,000 pounds and occupying about 300 cubic feet. Previous approaches have generally operated maximum-sized amplifiers at maximum-power and amplifying longer-and-longer pulses.

In one embodiment, the man-portable unit is used in a hospital and includes a handheld probe, a vest, control-cart and receive power from a wall plug. In one embodiment, the handheld probe contains beam-scanners and optical delivery fibers. In one embodiment, the vest contains optical compressors and the optical amplifiers are positioned in the cart. In one embodiment, the cart contains the control module, the control panel, the pulse generator, the power supplies, a video camera, a video monitor, air flush system, a suction system and a marker beam generator.

In one embodiment, the optical-fiber-containing umbilical cables are used between components. In one embodiment, the umbilical includes a hollow ablation fiber for pulses compressed to sub-picosecond duration. One embodiment, the fiber is a hollow optical fiber, a video-camera fiber, an illumination fiber, a marker-beam fiber, an air flush tube, a suction tube and wiring for the scanners.

One embodiment is battery-powered and contains a probe, vest, backpack and one or more satchels. In one embodiment, the handheld probe contains beam-scanners and optical delivery fibers. One embodiment includes a vest containing optical compressors, optical amplifiers and control devices. In one embodiment, the control devices are control knobs, switches, buttons, dial or pad, positioned in or on the cart. In one embodiment, the backpack contains the control module, the pulse generator, the power supplies, a marker beam generator, and a battery pack. In one embodiment, the satchel contains a video camera, a video monitor, an illumination source, and additional batteries. One embodiment is operable without the satchel. Another embodiment includes the video camera in the backpack and a heads-up display providing a video monitor and a display of control settings.

In one embodiment, the handheld probe contains piezo-electrically-driven-mirror beam-scanners and optical delivery fibers. In one embodiment, the delivery fiber has a lens on the fiber-end near the probe tip and transmits a video image back to the video camera. In another embodiment, a fiber illuminates the ablation region. In another embodiment, a hollow optical fiber brings ablation pulses to the beam-scanner mirrors. In another embodiment, a fiber is used to bring a laser marker beam to the beam-scanner mirrors. In another embodiment, the marker beam is scanned. In one embodiment, the laser marker beam shows the entire scan area, however other embodiments turn the beam off and on by the specifications of area, color and distance from target. Another embodiment shows the area that would be ablated if the ablation beam were on. In other embodiments, the marker beam changes color to indicate whether the ablation beam is on or off. In another embodiment, the probe contains tubes for suction and/or gas flush.

One embodiment, the man-portable units includes a handheld probe, handheld probe, vest/backpack and one or more satchels. The unit can be relatively inexpensive and can be used by surgeons, doctors, dentists, scientists and emergency personnel in the field. However, those skilled in the art will recognize other uses for the invention. In one embodiment, the unit can be used to cut a victim and cauterize wounds. In another embodiment, the system uses microsecond long, thermally-inducing, pulses to cauterize a wound. One embodiment can be used to perform emergency cutting of a victim or an object, removal of material, etching, marking and cauterizing of wounds. One embodiment allows the beam to cut through any obstacles. In one embodiment, the system can be used to gain access, open, cut into, or other wise free a person of object. One embodiment can be used to cut the top of a vehicle, I-beam, wood, metal, plastic, carbon fiber, cloth or fiberglass.

One embodiment uses one or more optically-pumped amplifiers of moderate-power, with a short optical pulse that is amplified and then compressed into a short pulse with the light pulse focused onto a small area spot. One embodiment of the present invention rapidly scans the spot over an area to be ablated and controls the pulse power to maximize ablation efficiency.

One embodiment controls the ablation rate and controls the pulse energy density in the ablation spot. If the spot size is fixed or otherwise known, this can be achieved by controlling pulse energy; or if the pulse energy is known, by controlling spot size. In one embodiment using optically-pumped amplifiers, the pulse energy is controlled step-wise by controlling repetition rate and fine-tuned by controlling optical pumping power. In another embodiment, the pulse energy of a semiconductor optical amplifier (SOA) is adjusted by changing the current thru the amplifier.

Further, it is preferred that ablation rate be controllable independent of pulse energy. One embodiment allows step wise control of the ablation rate independent of pulse energy through using two or more amplifiers in parallel a train mode (pulses from one amplifier being delayed to arrive one or more nanoseconds after those from another amplifier). Other embodiments allow a lower ablation rates by shutting off one or more amplifiers (e.g., the optical pumping to the fiber amplifier shut off), whereby there will be fewer pulses per train. One embodiment uses 20 amplifiers producing a maximum of 20 pulses in a train, however other embodiments use three or four amplifiers producing three or four pulses per train.

Generally, the optical amplifiers are pumped by laser diodes operating quasi-continually and are amplifying about 100,000 times per second for one nanosecond pulses. One embodiment uses optical amplifiers pumped by laser diodes. Another embodiment uses non-CW-pumping in operating amplifiers, whereby the amplifiers run in a staggered fashion, e.g., on for a first one second period and then turned off for one second period, and a first-period-dormant amplifier turned on during the second period, and so forth, to spread the heat load.

In some embodiments, the system is man-portable and includes a wheeled cart or a backpack. As used herein, the term "man-portable" means a system utilizing an optical amplifier that is either an optically-pumped-amplifier or a SOA with components that can be positioned by one man (e.g., as opposed to being mounted on a optical bench weighing hundreds of pounds), regardless of whether the system is designed to be easily moved or not. One embodiment includes an optically-pumped-amplifier with a compressor sized for a compression of between about ten picoseconds and about one nanosecond, or a SOA with a chirped-fiber-compressor, and which is designed to be reasonably easily moved.

One embodiment includes a method of ablative material removal, from a surface with a short optical pulse that is amplified and then compressed, including generating an initial pulse in a pulse generator within a man-portable system; amplifying the initial pulse and then compressing the amplified pulse within the man-portable system, wherein the amplifying and compression are done with either a fiber-amplifier and about ten picosecond and about one 1 nanosecond pulse-compressor combination, or a SOA and chirped fiber compressor combination; and applying the compressed optical pulse to the surface.

In one embodiment, the amplifying and compressing is accomplished with an optically-pumped-amplifier and air-path between gratings compressor combination. In one embodiment, the oscillator pulses are between about ten picoseconds and about one nanosecond. In another embodiment, the amplifying and compressing is done with a chirped fiber compressor combination. In one embodiment, the amplified pulses are between about one and about twenty nanoseconds in duration.

We have now found that certain laser-amplifier, compressor combinations enable practical, and significant size reduction, which in turn enables the system to be man-portable. One embodiment includes a man-portable system capable of being moved reasonably easily by one person. In one embodiment, the system includes a wheeled cart or possibly even being carried in a backpack, whereby the system is moveable from room to room. One embodiment uses initial pulses of between about ten picoseconds and about one nanosecond, with the initial pulse amplified by an optically-pumped-amplifier and compressed by an air-path between gratings compressor, with the compression creating a sub-picosecond ablation pulse. In one embodiment, the amplifier is an erbium-doped fiber amplifier or EDFA amplifier. In one embodiment, the grating compressor is a Treacy grating compressor.

Another embodiment uses a semiconductor optical amplifier (SOA) and a with a chirped fiber compressor. One embodiment uses pulses of between about one and about twenty nanoseconds during amplification. One embodiment uses a semiconductor generated initial pulse and a SOA preamplifier to amplify the initial pulse before introduction into the fiber amplifier.

While the compressors in either type of system can be run with inputs from more than one amplifier, reflections from other parallel (as used herein, "parallel" includes train mode) amplifiers can cause a loss of efficiency, and thus should be minimized. The loss is especially important if the amplifiers are amplifying signals at the same time, as is the case with the SOAs. In one embodiment each of the parallel SOAs has its own compressor, wherein the amplified pulses are then put into a single fiber after the compressors, whereby reflections from the joining (e.g., in a star connector) are reduced greatly before getting back to the amplifier. In one embodiment one or more fiber amplifiers are used with a single compressor, whereby the nanosecond spacing of sub-nanosecond pulses minimizes amplifying of multiple signals at the same time.

Fiber amplifiers have a storage lifetime of about 100 to 300 microseconds and for ablations purposes; fiber amplifiers have generally heretofore been operated with a time between pulses of almost equal to or greater than the storage lifetime, and thus are generally run a rep rate of less than 3-10 kHz. Fiber amplifiers are available with average power of 30 W or more. One embodiment uses a moderate-power 5 W average power fiber amplifiers producing pulses of about 500 microjoules or more to produce energy densities above the ablation threshold needed for non-thermal ablation, and increasing the energy in such a system, increases the ablation rate in either depth or allows larger areas of ablation or both.

In one embodiment an optically-pumped amplifier with a time between pulses of a fraction of the storage lifetime is used. In one embodiment, the optically-pumped amplifier with a time between pulses of about one-half or less of the storage lifetime. In one embodiment, a smaller spot is scanned to produce a larger effective ablation area. In one embodiment, the spot is about 50 microns or less in diameter. Other embodiments produce spots of about 60 or 75 microns or more. Spot sizes herein are given as circle diameter equivalents, a "50 micron" spot has the area of a 50 micron diameter circle, but the spot need not be round.

One embodiment uses parallel amplifiers to generate a train of pulses to increase the ablation rate by further increasing the effective repetition rate, whereby avoiding thermal problems. Another embodiment allows control of ablation rate by the use of a lesser number of operating fiber amplifiers. Another embodiment uses a SOA preamplifier to amplify the initial pulse before splitting to drive multiple parallel fiber amplifiers and another SOA before the introduction of the signal into each amplifier, whereby rapid shutting down of individual amplifiers can be achieved. Other embodiments operate with pulses at about three times the ablation threshold for greater ablation efficiency.

One embodiment uses about a 1 ns pulse with an optically-pumped amplifier and air optical-compressor to produce compression with approximately 40% losses. In one embodiment, the compressor is a Treacy grating compressor. At lower compressions, e.g., less than 1 nanosecond, the losses in a Treacy grating compressor are generally lower. If the other-than-compression losses are 10%, two nanoJoules are needed from the amplifier to get one nanoJoule on the target. One embodiment uses 1550 nm light. The use of greater than one nanosecond pulses in an air optical-compressor presents two problems; the difference in path length for the extremes of long and short wavelengths needs to be more three cm and, thus, the compressor is large and expensive, and the losses increase with a greater degree of compression.

Another embodiment uses a semiconductor optical amplifier (SOA) and a chirped fiber compressor is generally run with pulses of between about one and twenty nanosecond during amplification, and is operated at repetition rates with a time between pulses of more that the semiconductor storage lifetime. Another embodiment uses a SOA preamplifier to amplify the initial pulse before splitting to drive multiple SOAs. One embodiment scans a small ablation spot over a larger effective ablation area. In some embodiments with SOA Amplifiers a scanned spot that is smaller than the optically-pumped amplifier spot. One embodiment uses a semiconductor generated initial pulse.

Parallel amplifiers can be used to generate a train of pulses to increase the ablation rate by further increasing the effective repetition rate. Again, the pulse energy densities at operated at about three times the ablation threshold. One embodiment uses two or more amplifiers in parallel train mode, wherein pulses from one amplifier being delayed to arrive one or more nanoseconds after those from another amplifier. Other embodiments one or more amplifiers can be shut off producing fewer pulses per train. In one embodiment twenty amplifiers are used to produce a maximum of 20 pulses in a train, however, other embodiments use three or four amplifiers producing three or four pulses per train. In one embodiment, CW operation is used for operating amplifiers, wherein amplifiers might be run for e.g., one second and then turned off and a dormant amplifier turned on to spread the heat load.

In one embodiment controls the input optical signal power, optical pumping power of fiber amplifiers, timing of input pulses, length of input pulses, and timing between start of optical pumping and start of optical signals to control pulse power, and average degree of energy storage.

One embodiment includes an optical fibers have a maximum power of 4 MW, and thus, a 10-microJoule ablation pulse is amplified for a period as short as two picosecond. Thus, a fiber amplifier with this type of fiber can operates with an about ten ps, about 10 microjoule pulse, at 500 kHz (or 50 microjoule with 100 kHz). However, in embodiments where heating is a problem, multiple fiber amplifiers can be operated in a rotating mode. One embodiment rotates the operation of ten fiber amplifiers such that only five were operating at any one time (e.g., each on for $1/10^{th}$ of a second and off for $1/10^{th}$ of a second).

One embodiment includes ten optically-pumped amplifiers with time spaced inputs e.g., by 1 ns, to give a train of one to 0.10 pulses. One embodiment uses 5 W amplifiers operating at 100 kHz (and e.g., 50 microjoules) and step between 100 kHz and 1 MHz. With 50% post-amplifier optical efficiency and about 50 microjoules, to get. about six J/sq. cm on the target, the spot size would be about 20 microns.

One embodiment includes 20 amplifiers with time spaced inputs, e.g., by 1 ns, to giving a train of one to 20 pulses, 5 W amplifiers operating at 50 kHz (and e.g., 100 microjoules) this can step between 50 kHz and 1 MHz. With 50% post-amplifier optical efficiency and 100 microjoules, to get 6 J/sq. cm on the target, the spot size would be about 33 microns. The amplified pulse is between about 50 and about 100 picoseconds long. One embodiment includes 10 amplifiers at 50 kHz to step between 50 kHz and 500 kHz.

Generally, it is the pulse generator that controls the input repetition rate of the amplifiers to tune energy per pulse. Another embodiment includes 5 W amplifiers operating at 20 kHz (and e.g., 250 microjoules). With 10 amplifiers this can step between 20 kHz and 200 kHz. With 50% post-amplifier optical efficiency and 250 microjoules, to get 6 J/sq. cm on the target, the spot size would be about 50 microns. The amplified pulse is between 100 to 250 picoseconds long. Another embodiment includes 30 amplifiers that steps between 20 kHz and 600 kHz.

Although very-high power SOA's can be built, they are quite expensive and generally require large cooling systems. Therefore one embodiment uses a SOA with a lower power and a longer period of amplification, from about one and about twenty nanoseconds, and preferably between about five and about twenty nanoseconds. Air-grating compressors are impractically large at these time periods. Therefore one embodiment of the man-portable SOA amplifier systems uses chirped fiber gratings (such gratings are commercially available from 3M). Another embodiment uses fiber amplifiers and use chirped fiber gratings, whereby these fiber gratings can be shorter, with less compression than those used with our SOAs.

Another embodiment generates a sub-picosecond pulse and time stretching that pulse within semiconductor pulse generator to give the initial wavelength-swept-with-time pulse.

One embodiment uses light leakage from the delivery fiber to get feedback proportional to pulse power and/or energy for control purposes. One embodiment measures the spot size with a video camera or a linear scan. One embodiment uses an "in-vivo" type camera (see "Camera Containing Medical Tool," U.S. Provisional Patent Application Ser. No. 60/472,071 filed May 20, 2003 which is incorporated by reference herein). One embodiment includes a handheld beam-emitting probe that provides its own illumination. Other embodiments include cameras using an optical fiber in a probe to convey an image back to a remote camera body. Another embodiment includes a vidicon-containing camera with a GRIN fiber lens. Still other embodiments use endoscope type cameras.

One embodiment scans a smaller ablation area by moving the beam without moving the probe. Another embodiment scans a large area by moving the beam over a first area, and then stepping the probe to second portion of the large area and then scanning the beam over the second area, and so on. One embodiment uses beam deflecting mirrors mounted on piezoelectric actuators to move the beam (see "Scanned Small Spot Ablation With A High-Rep-Rate," U.S. Provisional Patent Application Ser. No. 60/471,972 filed May 20, 2003 which is incorporated by reference herein). One embodiment scans the actuators over a larger region but with the ablation beam only enabled to ablate portions with defined color and/or area. One embodiment allows evaluation after a prescribed time through preset combination of time and, area and/or color.

Information of such a system and other information on ablation systems are given in co-pending provisional applications listed in the following paragraphs (which are also at least partially co-owned by, or exclusively licensed to, the owners hereof) and are hereby incorporated by reference herein (provisional applications listed by docket No., title and U.S. Provisional Patent Application Ser. No.):

"Laser Machining," U.S. Provisional Patent Application Ser. No. 60/471,922;ABI-4 "Camera Containing Medical Tool," U.S. Provisional Patent Application Ser. No. 60/472,071;ABI-6 "Scanned Small Spot Ablation With A High-Rep-Rate," U.S. Provisional Patent Application Ser. No. 60/471,972;and ABI-7 "Stretched Optical Pulse Amplification and Compression," U.S. Provisional Patent Application Ser. No. 60/471,971;all filed May 20, 2003.

ABI-8 "Controlling Repetition Rate Of Fiber Amplifier," U.S. Provisional Patent Application Ser. No. 60/494,102; ABI-9 "Controlling Pulse Energy Of A Fiber Amplifier By Controlling Pump Diode Current," U.S. Provisional Patent Application Ser. No. 60/494,275;ABI-10 "Pulse Energy Adjustment For Changes In Ablation Spot Size," U.S. Provisional Patent Application Ser. No. 60/494,274;ABI-11. "Ablative Material Removal With A Preset Removal Rate or Volume or Depth," U.S. Provisional Patent Application Ser. No. 60/494,273; ABI-12 "Fiber Amplifier With A Time Between Pulses Of A Fraction Of The Storage Lifetime," U.S. Provisional Patent Application Ser. No. 60/494,272;ABI-14 "Controlling Temperature Of A Fiber Amplifier By Controlling Pump Diode Current," U.S. Provisional Patent Application Ser. No. 60/494,322;ABI-15 "Altering The Emission Of An Ablation Beam for Safety or Control," U.S. Provisional Patent Application Ser. No. 60/494,267;ABI-16 "Enabling Or Blocking The Emission Of An Ablation Beam Based On Color Of Target Area," U.S. Provisional Patent Application Ser. No. 60/494,172;ABI-17 "Remotely-Controlled Ablation of Surfaces," U.S. Provisional Patent Application Ser. No. 60/494,276;and ABI-18 "Ablation Of A Custom Shaped Area," U.S. Provisional Patent Application Ser. No. 60/494,180;were all filed Aug. 11, 2003.ABI-19 "High-Power-Optical-Amplifier Using A Number Of Spaced, Thin Slabs," U.S. Provisional Patent Application Ser. No. 60/497,404 was filed Aug. 22, 2003.

ABI-20 "Spiral-Laser On-A-Disc," U.S. Provisional Patent Application Ser. No. 60/502,879 and "Laser Beam Propagation in Air," U.S. Provisional Patent Application Ser. No. 60/502,886 were both filed on Sep. 12, 2003. ABI-22 "Active Optical Compressor," U.S. Provisional Patent Application Ser. No. 60/503,659 was filed Sep. 17, 2003.

ABI-24 "High Power SuperMode Laser Amplifier" U.S. Provisional Patent Application Ser. No. 60/505,968 was filed Sep. 25, 2003;ABI-25 "Semiconductor Manufacturing Using Optical Ablation," U.S. Provisional Patent Application Ser. No. 60/508,136 was filed Oct. 2, 2003;ABI-26 "Composite Cutting With Optical Ablation Technique," U.S. Provisional Patent Application Ser. No. 60/510,855 was filed Oct. 14, 2003; and ABI-27 "Material Composition Analysis Using Optical Ablation," U.S. Provisional Patent Application Ser. No. 60/512,807 was filed Oct. 20, 2003.

ABI-28 "Quasi-Continuous Current in Optical Pulse Amplifier Systems," U.S. Provisional Patent Application Ser. No. 60/529,425 and ABI-29 "Optical Pulse Stretching and Compressing," U.S. Provisional Patent Application Ser. No. 60/529,443, were both filed Dec. 12, 2003.

ABI-30 "Start-up Timing for Optical Ablation System," U.S. Provisional Patent Application Ser. No. 60/539,026; ABI-31 "High-Frequency Ring Oscillator," U.S. Provisional Patent Application Ser. No. 60/539,024;and ABI-32 "Amplifying of High Energy Laser Pulses," U.S. Provisional Patent Application Ser. No. 60/539,025 were all filed Jan. 23, 2004.

ABI-33 "Semiconductor-Type Processing for Solid-State Lasers," U.S. Provisional Patent Application Ser. No. 60/543,086,was filed Feb. 9, 2004. ABI-34 "Pulse Streaming of Optically-Pumped Amplifiers," U.S. Provisional Patent Application Ser. No. 60/546,065,was filed Feb. 18, 2004.ABI-35 "Pumping of Optically-Pumped Amplifiers," U.S. Provisional Patent Application Ser. No. 60/548,216 was filed Feb. 26, 2004.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification, but only by the claims.

What is claimed is:

1. A system comprising:
   a pulse generator configured for generating pulses;
   a man-portable amplifier and compressor combination configured for amplifying the pulses and compressing the pulses, to generate amplified compressed pulses,
      wherein the amplifier and the compressor combination comprises an optically-pumped-amplifier and air-path between gratings compressor combination; and
   a handheld probe configured for applying the amplified compressed pulses to an object in order to remove material therefrom.

2. The system of claim 1 wherein the object is a body and the handheld probe is configured to apply the amplified compressed pulses to an interior of the body.

3. The system of claim 1 wherein pulse energy density and ablation rate are independently controlled.

4. The system of claim 1 wherein the pulse generator is semiconductor oscillator-driven.

5. The system of claim 1 further comprising a vest configured to carry the compressor and a cart configured to carry the amplifier.

6. The system of claim 5 wherein the cart is configured to carry the pulse generator and further configured to carry a control module.

7. The system of claim 1 wherein the handheld probe contains a beam-scanner and an optical delivery fiber.

8. The system of claim 1 further comprising a vest and a backpack.

9. The system of claim 8 wherein the vest is configured to carry the compressor.

10. The system of claim 8 wherein the backpack is configured to carry the pulse generator.

11. The system of claim 8 further comprising a satchel configured to carry a video monitor.

12. The system of claim 8 further comprising a heads-up display providing a video monitor and a display of control settings.

13. A system comprising:
    a pulse generator configured for generating pulses;
    a man-portable amplifier and compressor combination configured for amplifying the pulses and compressing the pulses, to generate amplified compressed pulses,
       wherein the amplifier and the compressor combination comprises a semi-conductor optical amplifier and chirped fiber compressor combination; and
    a handheld probe configured for applying the amplified compressed pulses to an object in order to remove material.

14. The system of claim 13 wherein the object is a body and the handheld probe is configured to apply the amplified compressed pulses to an interior of the body.

15. The system of claim 13 wherein pulse energy density and ablation rate are independently controlled.

16. The system of claim 13 wherein the pulse generator is semiconductor oscillator-driven.

17. The system of claim 13 further comprising a vest configured to carry the compressor and a cart configured to carry the amplifier.

18. The system of claim 13 wherein the cart is configured to carry the pulse generator and further configured to carry a control module.

19. The system of claim 13 wherein the handheld probe contains a beam-scanner and an optical delivery fiber.

20. The system of claim 13 further comprising a vest and a backpack.

21. The system of claim 20 wherein the vest is configured to carry the compressor.

22. The system of claim 20 wherein the backpack is configured to carry the pulse generator.

23. The system of claim 20 further comprising a satchel configured to carry a video monitor.

24. The system of claim 20 further comprising a heads-up display providing a video monitor and a display of control settings.

* * * * *